US008765813B2

(12) United States Patent
Wade et al.

(10) Patent No.: US 8,765,813 B2
(45) Date of Patent: Jul. 1, 2014

(54) USE OF TREPROSTINIL TO TREAT AND PREVENT ISCHEMIC LESIONS

(75) Inventors: Michael Wade, Chapel Hill, NC (US); Roger Jeffs, Chapel Hill, NC (US); Robert Roscigno, Chapel Hill, NC (US); Deborah Strootman, Tucson, AZ (US); Kathryn Bronstein, Jupiter, FL (US)

(73) Assignee: United Therapeutics Corporation, Silver Spring, MD (US)

( * ) Notice: Subject to any disclaimer, the term of this patent is extended or adjusted under 35 U.S.C. 154(b) by 2096 days.

(21) Appl. No.: 11/012,723

(22) Filed: Dec. 16, 2004

(65) Prior Publication Data

US 2005/0165111 A1      Jul. 28, 2005

Related U.S. Application Data

(60) Provisional application No. 60/529,622, filed on Dec. 16, 2003.

(51) Int. Cl.
*A61K 31/19* (2006.01)
*A61K 38/00* (2006.01)
*A61K 33/40* (2006.01)

(52) U.S. Cl.
USPC ......................................................... 514/571

(58) Field of Classification Search
USPC ......... 424/305, 311, 317, 318, 331, 337, 339, 424/393, 613; 514/12, 571, 18.6; 530/399
See application file for complete search history.

(56) References Cited

U.S. PATENT DOCUMENTS

| | | | |
|---|---|---|---|
| 4,254,145 A * | 3/1981 | Birnbaum | ..................... 514/530 |
| 4,281,113 A | 7/1981 | Axen et al. | |
| 4,306,075 A | 12/1981 | Aristoff | |
| 4,306,076 A | 12/1981 | Nelson | |
| 4,338,457 A | 7/1982 | Aristoff | |
| 4,349,689 A | 9/1982 | Aristoff | |
| 4,486,598 A | 12/1984 | Aristoff | |
| 4,668,814 A | 5/1987 | Aristoff | |
| 4,683,330 A | 7/1987 | Aristoff | |
| 4,692,464 A | 9/1987 | Skuballa et al. | |
| 4,708,963 A | 11/1987 | Skuballa et al. | |
| 4,895,719 A | 1/1990 | Radhakrishnan et al. | |
| 5,153,222 A | 10/1992 | Tadepalli et al. | |
| 5,190,972 A | 3/1993 | Dumble | |
| 5,234,953 A | 8/1993 | Crow et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,756,033 B2 | 6/2004 | Cloutier et al. | |
| 7,417,070 B2 | 8/2008 | Phares et al. | |
| 7,544,713 B2 | 6/2009 | Phares et al. | |
| 2002/0019350 A1 * | 2/2002 | Levine et al. | ................... 514/12 |
| 2004/0105819 A1 | 6/2004 | Hale et al. | |
| 2004/0265238 A1 | 12/2004 | Chaudry | |

FOREIGN PATENT DOCUMENTS

| | | |
|---|---|---|
| AU | 1999959533 B2 | 2/2000 |
| CA | 1 201 712 A | 3/1986 |
| EP | 0 159 784 A1 | 10/1985 |
| EP | 0 159 784 B1 | 6/1989 |
| EP | 0 347 243 A1 | 12/1989 |
| EP | 1 161 234 B1 | 12/2001 |
| GB | 2 070 596 A | 9/1981 |
| JP | 56-138130 A | 10/1981 |
| JP | 60-208936 A | 10/1985 |
| JP | 02-040325 A | 2/1990 |
| JP | 2003-523935 A | 8/2003 |
| WO | WO 99/25357 A | 5/1999 |
| WO | WO 00/54758 A2 | 9/2000 |
| WO | WO 00/57701 A1 | 10/2000 |
| WO | WO 2004/019952 A | 3/2004 |
| WO | WO 2005/007081 A | 1/2005 |

OTHER PUBLICATIONS

Vippagunta et al, Crystalline Solids, Advanced Drug Delivery Reviews, vol. 48, pp. 3-26, 2001.*
Engel et al, Treprostinil for the treatment of severe digital necrosis in systemic sclerosis, Vascular Medicine, vol. 10, pp. 29-32, 2005.*
Hummers et al. (Rheum Dis Clin North Am, vol. 29, No. 2, Abstract; May 2003).*
Wigley et al. (J Rheumatol, vol. 19, No. 9, Abstract; 1992).*
Skyscape reference [Retrieved on Dec. 3, 2010 from the Internet: <URL: http://mediwire.skyscape.com/main/Defaultaspx?P=Content&ArticleID=26317].*
Shigematsu et al. (International Angiology, vol. 18, No. 1, Abstract; Mar. 1999).*
Benthin, N. P., "Ilomedin (iloprost) og mb. Buerger". Ugeskr Laeger, vol. 157, No. 36, pp. 4946-4947 (1995).*
Clapp, L. H., et al., "Differential Effects of Stable Prostacyclin Analogs on Smooth Muscle Proliferation and Cyclic AMP Generation in Human Pulmonary Artery", Am. J. Respir. Cell Mol. Biol., vol. 26, pp. 194-201 (2002).
Fiessinger, J. N., et al., "Trial of iloprost versus aspirin treatment for critical limb ischaemia of thromboangiitis obliterans", The Lancet, vol. 335, No. 8689, pp. 555-557 (1990).
Kyle, M. V., et al., "Placebo Controlled Study Showing Therapeutic Benefit of Iloprost in the Treatment of Raynaud's Phenomenon", The Journ. Of Rheumatol., vol. 19, No. 9, pp. 1403-1406 (1992).
McHhugh, N. J., et al., "Infusion of Iloprost, a prostacyclin analogue, for treatment of Raynaud's phenomenon in systemic sclerosis", Annuals of the Rheumatic Diseases, vol. 47, No. 1, pp. 43-47 (1988).
Mills, Sr., J. L., "Buerger's Disease in the $21_{st}$ Century: Diagnosis, Clinical Features, and Therapy", Seminars in Vascular Surgery, vol. 16, No. 3, pp. 179-189 (2003).

(Continued)

Primary Examiner — Raymond Henly, III
(74) Attorney, Agent, or Firm — Foley & Lardner LLP

(57) ABSTRACT

The present disclosure relates to novel methods for using treprostinil or its derivative, or a pharmaceutically acceptable salt thereof, for the treatment and/or prevention of ischemic lesions, such as digital ulcers, in subjects with scleroderma (including systemic sclerosis), Buerger's disease, Raynaud's disease, Raynaud's phenomenon and/or other conditions that cause such lesions. The disclosure also relates to kits for treatment and/or prevention of ischemic lesions, which include an effective amount of treprostinil or its derivative, or a pharmaceutically acceptable salt thereof.

41 Claims, 8 Drawing Sheets

(56) References Cited

OTHER PUBLICATIONS

Mohler, III, E. R., et al., "Trial of a novel prostacyclin analog, UT-15, in patients with severe intermittent claudication", Vascular Medicine, vol. 5, pp. 231-237 (2000).
Norgren, L., et al., "A Stable Prostacycline Analogue (Iloprost) in the Treatment of Ischaemic Ulcers of the Lower Limb", Eur. J. Vasc. Surg., vol. 4, pp. 463-467 (1990).
Olin, J. W., "Thromboangiitis Obliterans (Buerger's Disease)", The New Engl. J. Med., vol. 343, No. 12, pp. 864-869 (2000).
Patterson, J. H., et al., "Acute Hemodynamic Effects of the Prostacyclin Analog 15AU81 in Severe Congestive Heart Failure", The Amer. J. Card., vol. 75, pp. 26A-33A (1995).
Raychaudhuri, B., et al., "The Prostacyclin Analogue Treprostinil Blocks NFκB Nuclear Translocation in Human Alveolar Macrophages", J. Biol. Chem., vol. 277, No. 36, pp. 33344-33348 (2002).
Shionoya, S., "Diagnostic criteria of Buerger's disease", Intl. J. Cardio. 66 (Suppl. 1), pp. S243-S245 (1998).
Tyle, P., "Iontophoretic Devices for Drug Delivery", Pharma. Res., vol. 3, No. 6, pp. 318-326 (1986).
Brock et al., "Iloprost in der Behandlung ischämischer Gewebsläsionen bei Diabetikern," Schweiz. Med. Wschr., 1990, 120(40):1477-1482, with English summary.
Creutzig et al., "Prostanoids in therapy of peripheral arterial occlusive disease," Therapie, 1991, 46:241-245, with English summary.
Fink et al., "Use of Prostacyclin and its Analogues in the Treatment of Cardiovascular Disease," Heart Disease, 1999, 1:29-40.
Mueller et al., "Potential therapeutic mechanisms of stable prostacyclin ($PGI_2$)-mimetics in severe peripheral vascular disease," Biomed. Biochim. Acta, 1988, 47(Oct. 2011):S40-S44.
O'Meara et al., "Systematic reviews of wound care management: (3) antimicrobial agents for chronic wounds; (4) diabetic foot ulceration," Health Technology Assessment, 2000, 4(21):15-228.
Zwicke et al., "Treprostinil sodium for management of wounds refractory to standard therapy secondary to critical limb ischemia," Wounds, Mar. 2007, 19(3):A31.
Zwicke et al., "Treprostinil sodium for management of wounds refractory to standard therapy secondary to critical limb ischemia: an extension study," Wounds, Mar. 2007, 19(3):A32.
Office Action dated Jan. 25, 2011, in corresponding Japanese Application No. 2006-545436, with English translation, 4 pages.
Booke et al., "Prostaglandins in Patients with Pulmonary Hypertension: The Route of Administration," Anesth. Analg., Letters to the Editor, 1998, 86:917.
Hummers et al,. "Management of Raynaud's phenomenon and digital ischemic lesions in scleroderma," Rheum. Dis. Clin. North Amer., May 2003, 29(2):293-313, full article.
Shigematsu et al,. "Factors affecting the long-term outcome of Buerger's disease (thromboangiitis obliterans)," International Angiology, Mar. 1999, 18(1):58-64, full article.
Wigley et al., "Intravenous iloprost treatment of Raynaud's phenomenon and ischemic ulcers secondary to systemic sclerosis," J. Rheumatol., Sep. 1992, 19(9):1407-1414, full article.
Norgren et al,. "Inter-Society Consensus for the Management of Peripheral Arterial Disease (TASC II)," J. Vasc. Surg., Jan. 2007, S5A-S67A.
Chattaraj, Sarat C., "Treprostinil sodium Pharmacia," Current Opinion in Investigational Drugs, Apr. 2002, 3(4):582-586.
Langevitz et al., "Treatment of Refractory Ischemic Skin Ulcers in Patients with Raynaud's Phenomenon with $PGE_1$, Infusions," The Journal of Rheumatology, 1989, 16(11):1433-1435.
Nizankowski et al., "Prostacyclin for Ischemic Ulcers in Peripheral Arterial Disease. A Random Assignment, Placebo Controlled Study," Thrombosis Research, 1985, 37:21-28.
Abe et al., "Effects of inhaled prostacyclin analogue on chronic hypoxic pulmonary hypertension," J. Cardiovascular Pharmacology, 2001, 37, 239 251.
Bein et al., "Cardiovascular and pulmonary effects of aerosolized prostacyclin administration in severe respiratory failure using a ventilator nebulization system," J. Cardiovascular Pharmacology, 1996, 27, 583-586.
Benedict et al., "Evidence-based pharmacologic management of pulmonary arterial hypertension," Clinical Therapeutics, 2007, 29, 2134-2153.
Bindl et al., "Aerosolised prostacyclin for pulmonary hypertension in neonates," Archives of disease in childhood, Fetal and neonatal edition, 1994, 71(3), F214-6.
Channick et al., "Safety and efficacy of inhaled treprostinil as add-on therapy to bosentan in pulmonary arterial hypertension," J. American College of Cardiology, 2006, 48, 1433-1437.
Dumas et al,. "Hypoxic pulmonary vasoconstriction," General Pharmacology, 1999, 33, 289-297.
Dworetz et al., "Survival of infants with persistent pulmonary hypertension without extracorporeal membrane oxygenation," Pediatrics, 1989, 84, 1-6.
Ewert et al., "Iloprost als inhalative bzw. Intravenose langzeitbehandlung von patienten mit primarer pulmonaler hypertonie," Z. Kardiol., 2000, 89, 987-999.
Ewert et al., "Aerosolized iloprost for primary pulmonary hypertension," New England Journal of Medicine, 2000, 343, 1421-1422.
Gessler et al., "Ultrasonic versus jet nebulization of iloprost in severe pulmonary hypertension," Eur. Respir. J., 2001, 17, 14-19.
Haraldsson et al., "Comparison of inhaled nitric oxide and inhaled aerosolized prostacyclin in the evaluation of heart transplant candidates with elevated pulmonary vascular resistance," Chest, 1998, 114, 780-786.
Hoeper et al., "Effects of inhaled nitric oxide and aerosolized iloprost in pulmonary veno-occlusive disease," Respiratory Medicine, 1999, 93, 62-70.
Hoeper et al., "A comparison of the acute hemodynamic effects of inhaled nitric oxide and aerosolized iloprost in primary hypertension," J. American College of Cardiology, 2000, 35, 176-182.
Hoeper et al., "Long term treatment of primary pulmonary hypertension with aerosolized iloprost, a prostacyclin analogue," New England Journal of Medicine, 2000, 342, 1866-1870.
Howarth, P.H., "Why particle size should affect clinical response to inhaled therapy," Journal of Aerosol Medicine, 2001, 14 Supp. 1, S-27-S-34.
Ichida et al., "Additive effects of beraprost on pulmonary vasodilation by inhaled nitric oxide in children with pulmonary hypertension," American Journal of Cardiology, 1997, 80, 662-664.
Krause et al., "Pharmacokinetics and pharmacodynamics of the prostacyclin analogue iloprost in man,".Eur. J. Clin. Pharmacol., 1986, 30, 61-68.
Lee et al., "Current strategies for pulmonary arterial hypertension," J. Internal Medicine, 2005, 258, 199-215.
Max et al., "Inhaled prostacyclin in the treatment of pulmonary hypertension," Eur. J. Pediatr., 1999, 158 Suppl 1, S23-S26.
Olschewski et al., Aerosolized prostacyclin and iloprost in severe pulmonary hypertension,: Annals of Internal Medicine, 1996, 124, 820 824.
Olschewski et al., "Recovery from circulatory shock in severe primary pulmonary hypertension (PPH) with aerosolization of iloprost," Intensive Care Med., 1998, 24, 631-634.
Olschewski et al., "Inhaled prostacyclin and iloprost in severe pulmonary hypertension secondary to lung fibrosis," Am. Respir. Crit. Care Med., 1999, 160, 600-607.
Olschewski et al. For the German PPH Study Group, "Inhaled iloprost to treat severe pulmonary hypertension—An uncontrolled trial," Annals of Internal Medicine, 2000, 132, 435-443.
Olschewski et al., "Pharmacodynamics and pharmacokinetics of inhaled iloprost, aerosolized by three different devices, in severe pulmonary hypertension," Chest, 2003, 124, 1294-1304.
Olschewski et al., "Prostacyclin and its analogues in the treatment of pulmonary hypertension,"Pharmacology and Therapeutics, 2004, 102, 139-153.
Santak et al., "Prostacyclin aerosol in an infant with pulmonary hypertension," Eur. J. Pediatr., 1995, 154, 233-235.
Soditt et al., "Improvement of oxygenation induced by aerosolized prostacyclin in a preterm infant with persistent pulmonary hypertension of the newborn," Intensive Care Med., 1997, 23, 1275-1278.

(56) References Cited

OTHER PUBLICATIONS

Stricker et al., "Sustained improvement of performance and haemodynamics with long-term aerosolized prostacyclin therapy in severe pulmonary hypertension," Schweiz Med. Wochenschr., 1999, 129, 923-927.

Van Heerden et al., "Inhaled aerosolized prostacyclin as a selective pulmonary vasodilator for the treatment of severe hypertension," Anaesthesia and Intensive Care, 1996, 24, 87-90.

Van Heerden et al., "Re: Delivery of inhaled aerosolized prostacyclin (IAP)," Anaesthesia and Intensive Care, 1996, 24, 624-625.

Voswinckel, R., Enke, B., Reichenberger, F., Kohstall, M., Kreckel, A., Krick, S., Gall, H., Gessler, T., Schmehl, T., Ghofrani, H.A., Schermuly, R.T., Grimminger, F., Rubin, L.J., Seeger, W. and Olschewski, H. Favorable effects of inhaled treprostinil in severe pulmonary hypertension. J. American College of Cardiology 2006, 48, 1672-1681.

Voswinckel et al., "Acute effects of the combination of sildenafil and inhaled treprostinil on haemodynamics and gas exchange in pulmonary hypertension," Pulmonary Pharmacology & Therapeutics, 2008, 21, 824-832.

Walmrath et al., "Effects of inhaled versus intravenous vasodilators in experimental pulmonary hypertension," Eur. Respir. J., 1997, 10, 1084-1092.

Wasserman et al., "Bronchodilator effects of prostacyclin (PGI2) in dogs and guinea pigs," European.Journal of Pharmacology, 1980, 66, 53-63.

Webb et al., "The use of inhaled aerosolized prostacyclin (IAP) in the treatment of pulmonary hypertension secondary to pulmonary embolism," Intensive Care Med., 1996, 22, 353-355.

Wensel et al., "Effects of iloprost inhalation on exercise capacity and ventilator efficiency in patients with primary pulmonary hypertension," Circulation, 2000, 101, 2388-2392.

Wetzel, R.C., "Aerosolized prostacyclin: in search of the ideal pulmonary vasodilator," Anesthesiology, 1995, 82, 1315-1317.

Zanen et al., "The optimal particle size for β-adrenergic aerosols in mild asthmatics," International Journal of Pharmaceutics, 1994, 107, 211-217.

Zanen et al., "Optimal particle size for beta 2 agonist and anticholinergic aerosols in patients with severe airflow obstruction," Thorax, 1996, 51, 977-980.

Reply Under 37 CFR 1.116 filed May 23, 2013, in U.S. Appl. No. 12/926,945.

Notice of Allowance mailed Jun. 18, 2013, in U.S. Appl. No. 12/926,945.

Aristoff et al., "Synthesis of benzopyran prostaglandins, potent stable prostacyclin analogs, via an intermolecular mitsunobu reaction," Tetrahedron Letters, 1984, 25(36):3955-3958.

Doyle et al., "Inhaled prostacyclin as a selective pulmonary vasodilator," Anaesthesia and Intensive Care, Aug. 1996, 24(4):514-515.

Dworetz et al., "Survival of Infants With persistent Pulmonary Hypertension Without Extracorporeal Membrane Oxygenation," Pediatrics, 1989, 84(1):1-6.

Fox et al., "Pulmonary Hypertension in the Perinatal Aspiration Syndromes," Pediatrics, 1977, 59(2):205-211.

Medterms.com (retrieved on Sep. 2, 2011 from the Internet: URL: http://www.medterms.com/script/main/art.asp?articlekey-10001).

Osmonics Pure Water Handbook, $2^{nd}$ Edition, 1991, 151 pages.

Pappert et al., "Aerosolized Prostacyclin Versus Inhaled Nitric Oxide in Children with Severe Acute Respiratory Distress Syndrome," Anesthesiology, Jun. 1995, 82(6):1507-1511.

Peckham et al., "Physiologic factors affecting pulmonary artery pressure in infants with persistent pulmonary hypertension," J. Pediatrics, 1978, 93(6):1005-1010.

Steffen et al., "The Effects of 15AU81, a Chemically Stable Prostacyclin Analog, on the Cardiovascular and Renin-Angiotensis Systems of Anesthetized Dogs, Prostaglandins, Leukotrienes and Essential Fatty Acids," 1991, 43:277-286.

Zapol et al., "Pulmonary Circulation During Adult Respiratory Distress Syndrome," Pulmonary Cicculation During ARDS, 1985, 241-273.

\* cited by examiner

Figure 1. Study design.
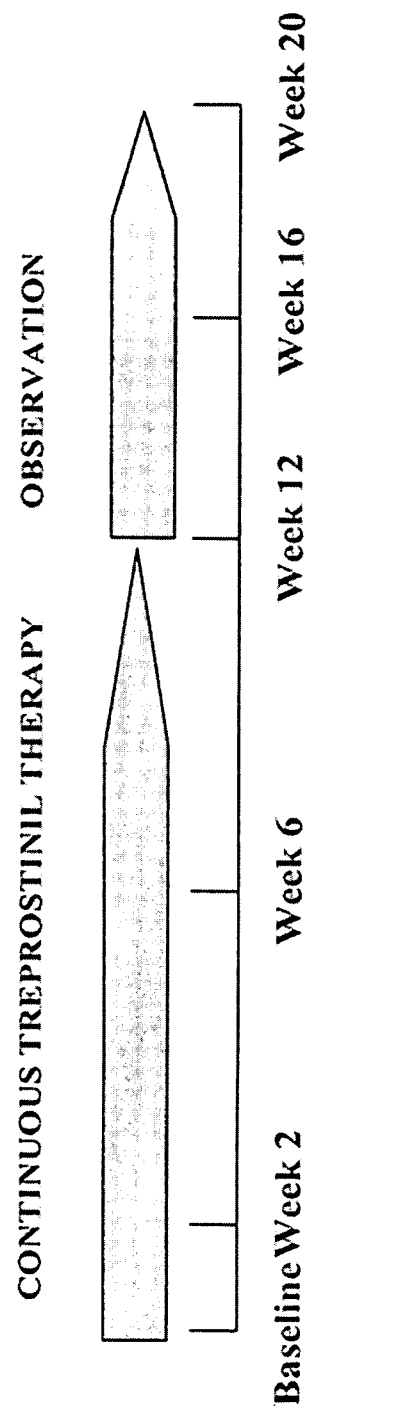

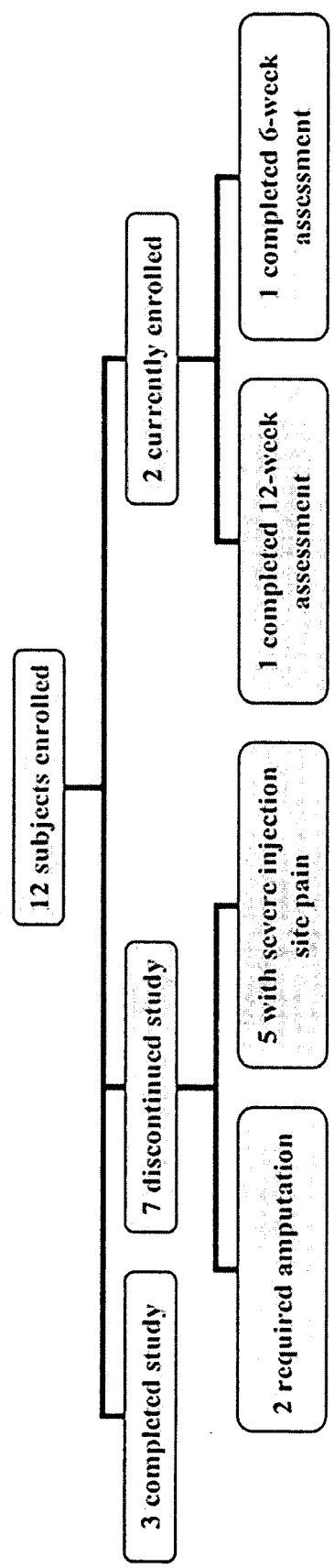
Figure 2. Disposition of patients enrolled.

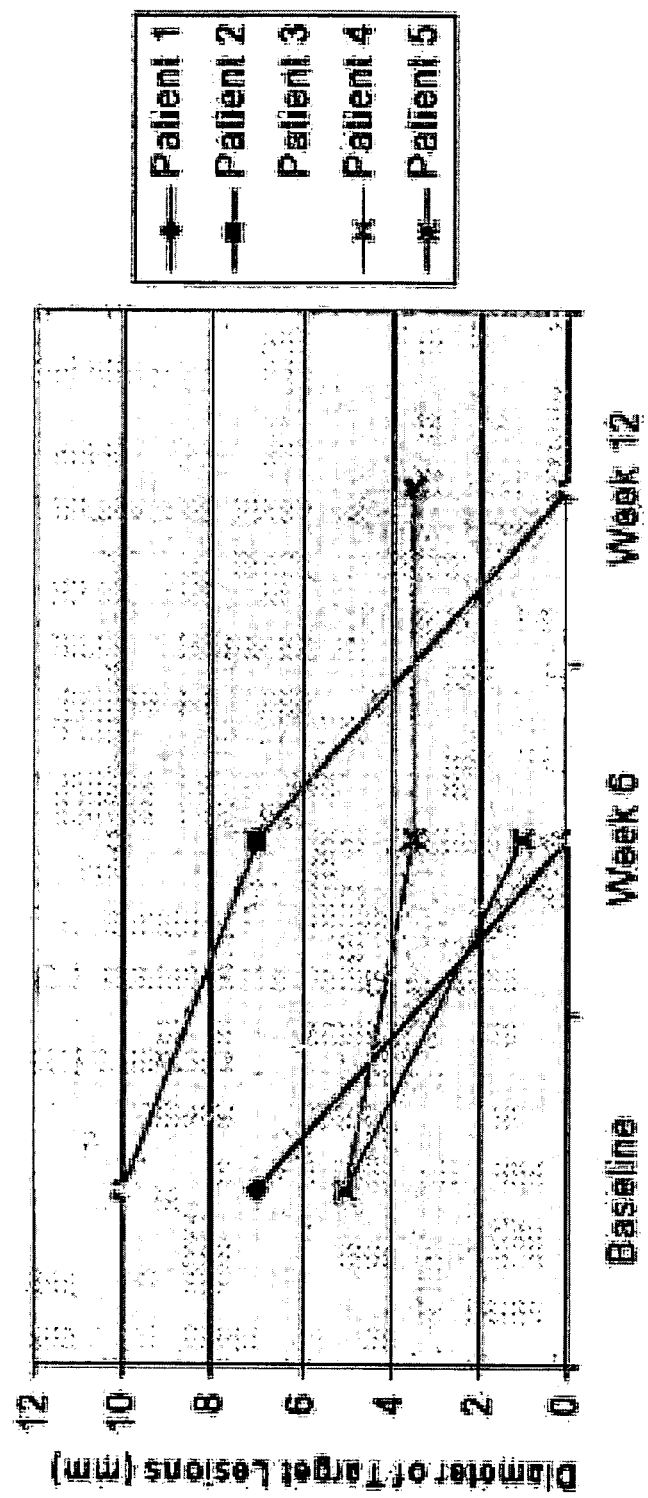

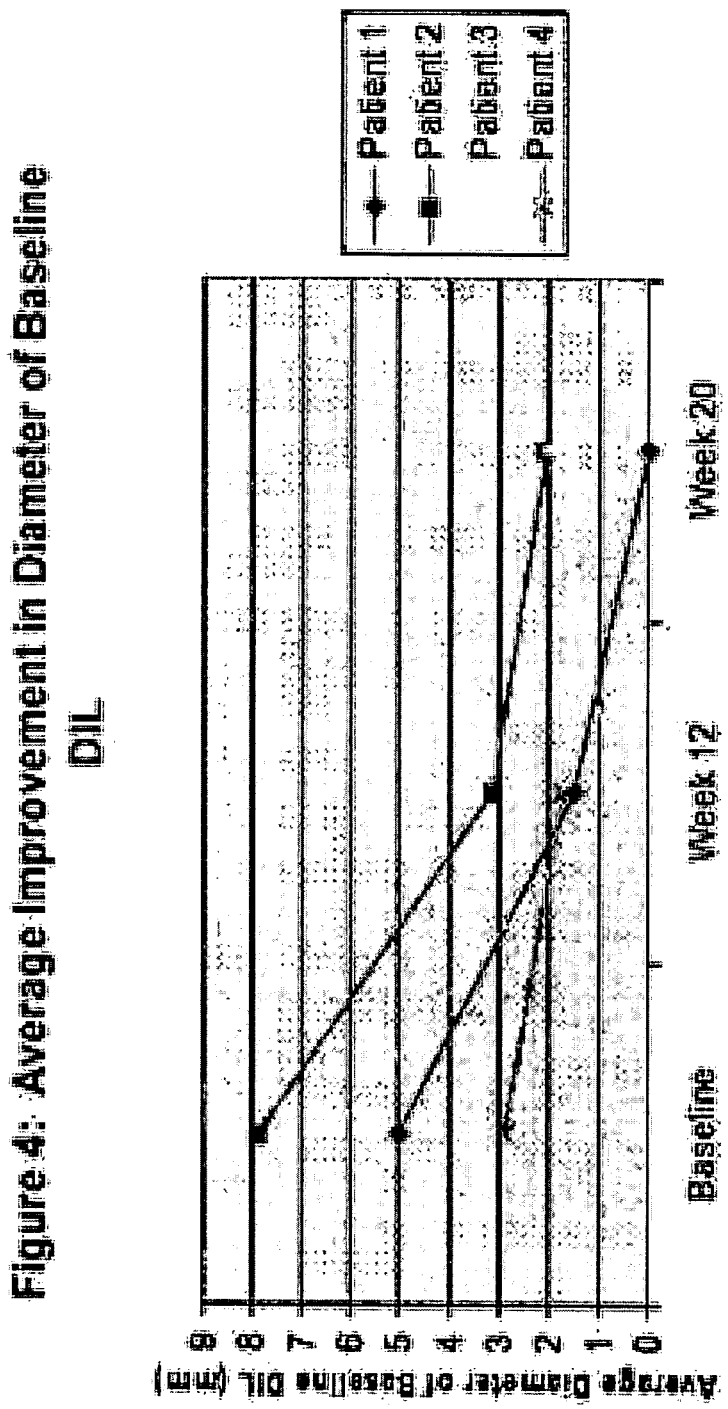

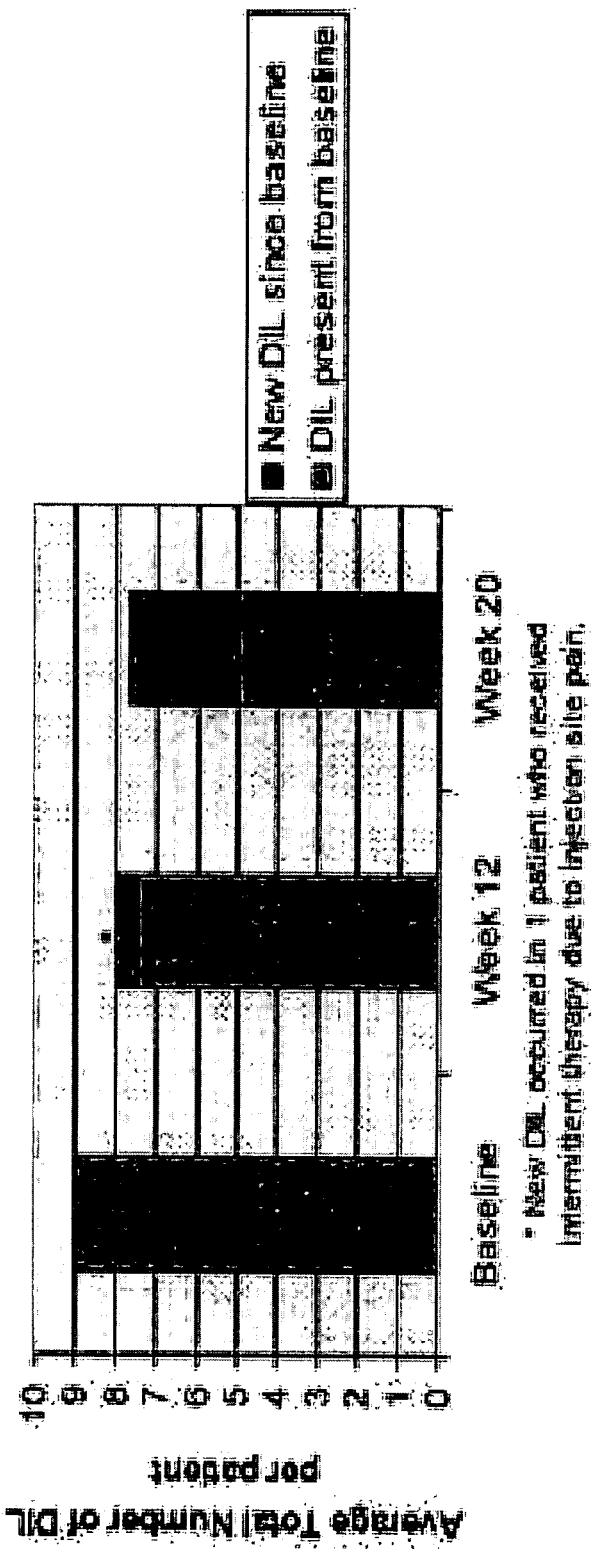

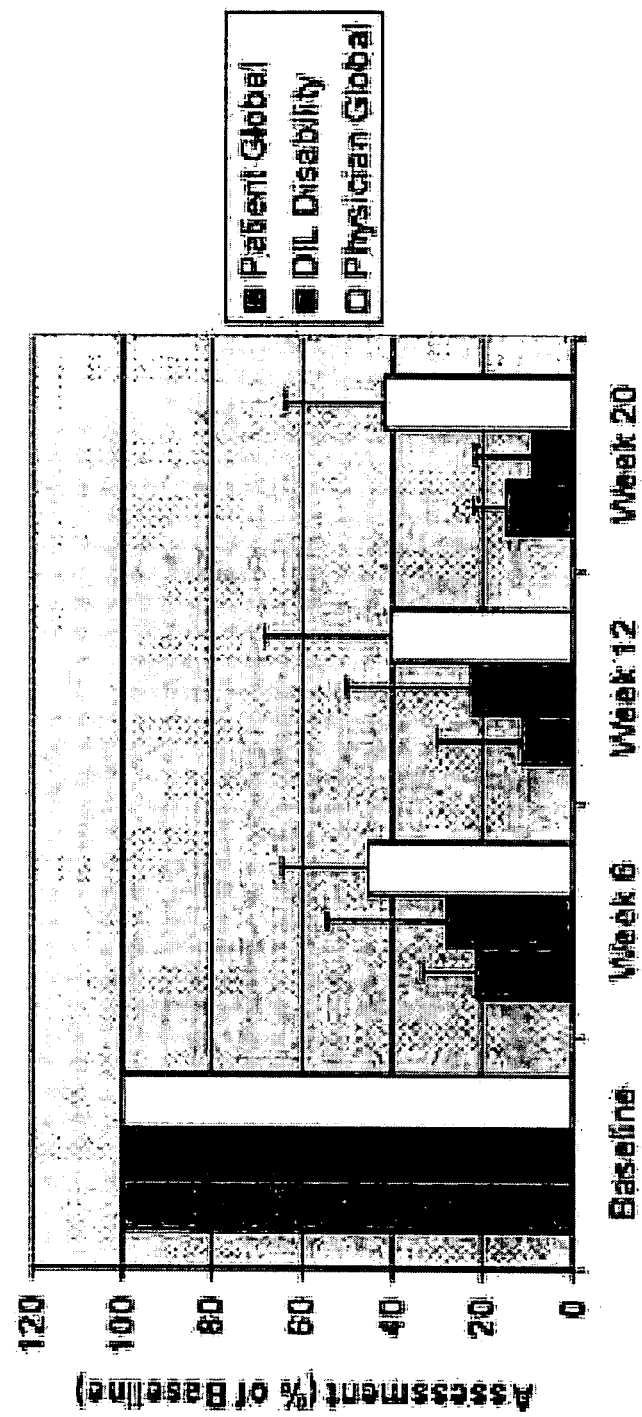

Figure 7. Resolution of target DIL overlying 3rd MCP

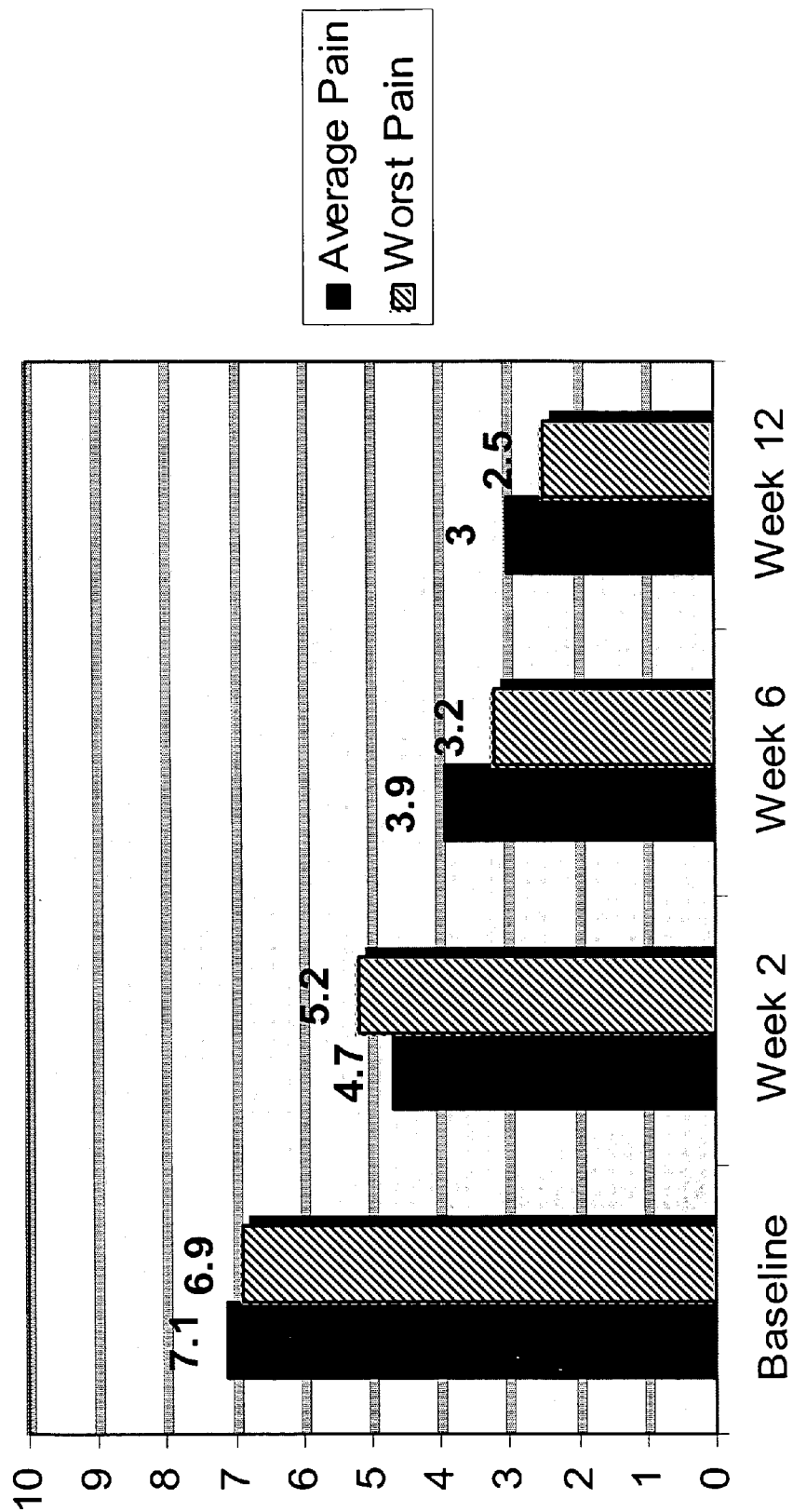
Figure 8. Mean and worst rest pain assessed by the patients.

USE OF TREPROSTINIL TO TREAT AND PREVENT ISCHEMIC LESIONS

FIELD OF INVENTION

The invention relates to the use of treprostinil or its derivative, or a pharmaceutically acceptable salt thereof, to treat and/or prevent ischemic lesions, such as digital (fingers and toes) ulcers and necrotic lesions, caused by scleroderma, diabetes, peripheral arterial disease, Buerger's disease, Raynaud's disease, Raynaud's phenomenon or other conditions. This invention also relates to kits to be used for this purpose.

BACKGROUND

Treprostinil, also known as UT-15, is a known compound disclosed in U.S. Pat. No. 4,306,075 in example 33. Treprostinil is a synthetic analog of epoprostenol, a prostaglandin $F_1$. The activities ascribed to the various compounds of this patent include inhibition of smooth muscle cell proliferation, inhibition of platelet aggregation, inhibition of cytokine secretion, reduction of gastric secretion, vasodialation and bronchodilation.

U.S. Pat. No. 5,153,222 discloses the use of treprostinil and related compounds to treat pulmonary hypertension. U.S. Pat. No. 6,054,486 discloses the use of treprostinil and related compounds to treat peripheral vascular disease, such as peripheral arterial occlusive disease and intermittent claudication. Patterson et al., *Amer. J. of Cardiology*, 75: 26A-33A (1995), have shown vasodilator effects of treprostinil in patients with class III or class IV heart failure.

Clapp et al., *Am. J. Respir. Cell. Mol. Biol.*, 26(2): 194-201 (2002), have shown that treprostinil inhibits proliferation of human pulmonary arterial smooth muscle cells. Raychaudhuri et al., *J. Biol. Chem.*, 277(36): 33344-8 (2002), have disclosed that treprostinil inhibits inflammatory cytokine (tumor necrosis factor-$\alpha$, interleukin-1$\beta$, interleukin-6, and granulocyte macrophage colony-stimulating factor) secretion and gene expression by human alveolar macrophages.

Patients with diseases or conditions, such as scleroderma (including systemic sclerosis), experience, among other things, abnormalities in the blood vessels that supply the skin. As a result, these patients experience ulcerations or even areas of necrosis (tissue death) on certain parts of their skin. Ischemic lesions associated with diseases such as scleroderma tend to occur on the hands and fingers, often over the knuckles, but also on other bony prominences, such as elbows, knees, hips, ankles and toes.

To date, the standard of care for treatment of ischemic lesions has included administration of topical hydrocolloid dressings, topical antibiotic ointments, analgesics for pain, debridement and wound care for ischemic wounds. Although certain types of dressings sometimes can help to aid healing of the lesions, the these treatments are often unsuccessful.

Other investigators have suggested that Ilomedin, a stable prostacyclin analog, may heal ischemic ulcers in lower limbs, as seen in patients with Buerger's disease. Fiessinger and Schafer, *Lancet*, 335(8689): 555-7 (1990); Norgren et al., *Eur. J. Vasc. Surg.* (5): 463-7 (1990); Benthin, *Ugeskr Laeger*, 157(36): 4946-7 (1995). Others have suggested that patients treated with Ilomedin treatment may show improvements in the frequency and severity of Raynaud's attacks. Kyle et al., *J Rheumatol.*, (9): 1403-6 (1992); McHugh et al., *Ann Rheum Dis.*, 47(1): 43-7 (1988).

Mohler et al., *Vascular Medicine*, 5: 231-237 (2000) have demonstrated, in patients with severe intermittent claudication, that treprostinil causes an increase in blood flow in large blood vessels of the lower limbs, such as the common femoral, superficial femoral, popliteal and anterial tibial arteries. These investigators also have found that treprostinil stimulates detectable blood flow in ankles of certain peripheral arterial disease patients, who otherwise exhibited minimal or no detectable blood flow in the absence of treatment. Likewise, the investigators found that some patients show improved pulse volume recordings in lower limbs upon treprostinil treatment.

Ischemic lesions, and particularly digital ischemic lesions, such as those caused by systemic schlerosis, are extremely painful, debilitating, and heal slowly. Thus, the need exists to identify viable methods, as well as kits, that can be used to prevent and treat such lesions. The present invention satisfies this need and provides related advantages as well.

SUMMARY

Administration of treprostinil or its derivatives, or pharmaceutically acceptable salts thereof, reduces the occurrence, number, size and severity of ischemic lesions, including digital ischemic lesions (such as ulcers and necrotic lesions), present on subjects with diseases such scleroderma, Buerger's disease, Raynaud's disease, Raynaud's phenomenon, and other conditions. Treprostinil is well suited for the prevention and treatment of ischemic lesions, including digital ischemic lesions, because the compound is a stable analogue of prostaglandin, can be used in intravenous administration, is not degraded when it passes through the lungs, and has a long biological half-life.

Accordingly, present invention provides for the treatment or prevention of ischemic lesions, such as digital ischemic lesions, in subjects with scleroderma (including systemic schlerosis), Buerger's disease, Raynaud's disease, Raynaud's phenomenon, or other conditions, comprising administering to a subject in need thereof an effective amount of treprostinil, its derivative or a pharmaceutically acceptable salt thereof. The present invention also provides for kits for accomplishing this purpose.

BRIEF DESCRIPTION OF THE FIGURES

FIG. 1 shows the design of a study that examines the use of treprostinil for the treatment and prevention of digital ischemic lesions in patients with systemic sclerosis.

FIG. 2 indicates the disposition of the patients enrolled in the study.

FIG. 3 is a graph showing the size of target lesions during treprostinil therapy.

FIG. 4 is a graph showing the average improvement in diameter of baseline digital ischemic lesions.

FIG. 5 is a bar graph showing the number of total and new digital ischemic lesions.

FIG. 6 is a bar graph showing the subjective measures of digital ischemic lesions FIG. 7 shows the resolution of target digital ischemic lesions overlying $3^{rd}$ metacarpophalangeal (MCP).

FIG. 8 shows a photograph of an injection site reaction.

DETAILED DESCRIPTION

The inventors believe that therapies that enhance cutaneous blood flow (i.e., to the skin), by increasing blood flow though smaller vessels and capillaries, are effective to treat and prevent ischemic lesions on the skin, including digital ischemic lesions. Prostacyclins are small molecules that have been previously shown to cause dilation of large blood vessels, relaxation of smooth muscle, inhibition of smooth muscle proliferation, as well as inhibition of platelet aggregation, which is involved in the blood clotting process. Similar actions by treprostinil at the microvascular level and on capillaries near the skin are believed to help enhance cutaneous blood flow and heal and/or prevent ischemia lesions or ulcers associated with scleroderma, Buerger's disease, Raynaud's disease, Raynaud's phenomenon, and other conditions.

The present invention relates to methods for treating and/or preventing ischemic lesions in a subject with a disease or condition that causes ischemic lesions, comprising administering to a subject in need thereof an effective amount of Treprostinil and/or a derivative thereof and/or a pharmaceutically acceptable salt thereof. Suitable derivatives include acid derivatives, pro-drugs, sustained release forms, inhaled forms and oral forms of Treprostinil, including those disclosed in U.S. Pat. No. 6,521,212 and co-pending Ser. No. 60/472,407, including oral forms comprising diethanolamine salt of treprostinil.

In one embodiment, the disease or condition that causes ischemic lesions comprises scleroderma, Buerger's disease, Raynaud's disease and/or Raynaud's phenomenon. In another embodiment, the ischemic lesions comprise digital ischemic lesions, such as finger ulcers and/or necrotic lesions. In another embodiment, the disease or condition that that causes ischemic lesions comprises systemic schlerois. In an additional embodiment, pain and/or other symptoms associated with digital ischemic lesions are reduced, eliminated or prevented upon administration of an effective amount of treprostinil and/or its derivatives, and/or pharmaceutically acceptable salts thereof.

The present invention also relates to kits for accomplishing such treatment or prevention of ischemic lesions. The invention includes a kit for treatment and/or prevention of ischemic lesions in a subject with a disease or condition that causes ischemic lesions, comprising (i) an effective amount of treprostinil or its derivatives, or pharmaceutically acceptable salts thereof, (ii) one or more pharmaceutically acceptable carriers and/or additives, and (iii) instructions for use in treating or preventing ischemic lesions. In one embodiment, the disease or condition that causes ischemic lesions comprises scleroderma, Buerger's disease, Raynaud's disease and/or Raynaud's phenomenon. In another embodiment, the ischemic lesions comprise digital ischemic lesions, such as finger ulcers and/or necrotic lesions. In another embodiment, the disease or condition that that causes ischemic lesions comprises systemic schlerois.

Unless otherwise specified, the term "a" or "an" used herein shall mean "one or more."

As used herein, the phrase "instructions for use" shall mean any FDA-mandated labeling, instructions, or package inserts that relate to the administration of treprostinil or its derivatives, or pharmaceutically acceptable salts thereof, for the purpose of treating or preventing ischemic lesions. For example, instructions for use may include, but are not limited to, indications for ischemic lesions, identification of specific symptoms associated with ischemic lesions, such as digital ulcers or pain, that can be ameliorated by treprostinil, and recommended dosage amounts for subjects suffering from ischemic lesions.

The term "acid derivative" is used herein to describe C1-4 alkyl esters and amides, including amides wherein the nitrogen is optionally substituted by one or two C1-4 alkyl groups.

The invention also includes bioprecursors or "pro-drugs" of treprostinil, that is, compounds which are converted in vivo to treprostinil or its pharmaceutically active derivatives thereof.

Further aspects of the present invention are concerned with the use of treprostinil or its derivatives, or pharmaceutically acceptable salts thereof, in the manufacture of a medicament for the treatment or prevention of ischemic lesions in subjects with Buerger's disease, scleroderma, Raynaud's disease, Raynaud's phenomenon, or other conditions.

The present invention also encompasses methods of using treprostinil or its derivatives, or pharmaceutically acceptable salts thereof. In one embodiment, a method uses treprostinil sodium, currently marketed under the trade name of REMODULIN®. The FDA has approved treprostinil sodium for the treatment pulmonary arterial hypertension by injection of dose concentrations of 1.0 mg/mL, 2.5 mg/mL, 5.0 mg/mL and 10.0 mg/mL. The chemical structure formula for treprostinil sodium is:

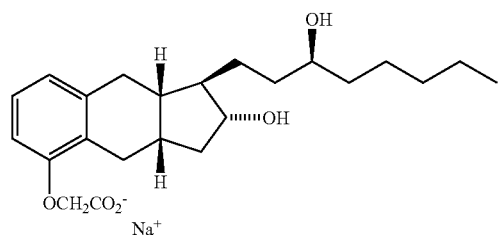

treprostinil sodium is sometimes designated by the chemical names: (a) [(1R,2R,3aS,9aS)-2,3,3a,4,9,9a-hexahydro-2-hydroxy-1-[(3S)-3-hydroxyoctyl]-1H-benz[f]inden-5-yl]oxy] acetic acid; or (b) 9-deoxy-2',9-a-methano-3-oxa-4,5,6-trinor-3,7-(1',3'-interphenylene)-13,14-dihydro-prostaglandin $F_1$. treprostinil sodium is also known as: UT-15; LRX-15; 15AU81; UNIPROST™; BW A15AU; and U-62,840. The molecular weight of treprostinil sodium is 390.52, and its empirical formula is $C_{23}H_{34}O_5$.

The present invention extends to methods of using physiologically acceptable salts of treprostinil, as well as non-physiologically acceptable salts of treprostinil that may be used in the preparation of the pharmacologically active compounds of the invention.

Physiologically acceptable salts of treprostinil include salts derived from bases. Base salts include ammonium salts (such as quaternary ammonium salts), alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

The amount of treprostinil or its derivative, or a pharmaceutically acceptable salt thereof, that is required in a medication or diagnostic aid according to the invention to achieve the desired effect will depend on a number of factors, such as the specific application, the nature of the particular compound used, the mode of administration, the concentration of the compound used, and the weight and condition of the patient.

A daily dose per patient for treatment or prevention of ischemic lesions may be in the range 25 µg to 250 mg; 0.5 µg to 2.5 mg, or 7 µg to 285 µg, per day per kilogram bodyweight. For example, an intravenous dose in the range 0.5 µg to 1.5 mg per kilogram bodyweight per day may conveniently be administered as an infusion of from 0.5 ng to 1.0 tag per kilogram bodyweight per minute. One possible dosage is 2.5 ng/kg/min, increased over 12 weeks by an amount of 2.50 ng/kg/min each week, until a target dose, such as 15 ng/kg/min, is reached. Infusion fluids suitable for this purpose contain, for example, from 10 ng to 1 tag per milliliter. Ampoules for injection contain, for example, from 0.1 tag to 1.0 mg and orally administrable unit dose formulations, such as tablets or capsules, contain, for example, from 0.1 to 100 mg, typically from 1 to 50 mg. For diagnostic purposes, a single unit dose formulation may be administered. In the case of physiologically acceptable salts, the weights indicated above refer to the weight of the active compound ion, that is, the ion derived from treprostinil.

In the manufacture of a medicament or diagnostic aid according to the invention, hereinafter referred to as a "formulation," treprostinil and/or its derivatives, and/or pharmaceutically acceptable salts thereof, may be admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.05% to 95% by weight of the active compound. One or more of treprostinil or its derivatives, or pharmaceutically acceptable salts thereof, may be incorporated in the formulations of the invention, which may be prepared by any of the well known techniques of pharmacy for admixing the components.

In addition to treprostinil, other pharmacologically active substances may be present in the formulations of the present invention which are known to be useful for treating ischemic lesions in subjects with scleroderma, Buerger's disease, Raynaud's disease, Raynaud's phenomenon, or other conditions. For example, the compounds of the invention may be present in combination with analgesics to treat pain, dressing changes, vasodilator medications, and topical or oral antibiotics.

The formulations of the invention include those suitable for parenteral (e.g., subcutaneous, intramuscular, intradermal, or intravenous), oral, inhalation (in solid and liquid forms), rectal, topical, buccal (e.g., sub-lingual) and transdermal administration, although the most suitable route in any given case may depend on the nature and severity of the condition being treated and on the nature of the particular form of treprostinil, its derivative, or a pharmaceutically acceptable salt thereof, which is being used.

Formulations of the present invention suitable for parenteral administration conveniently comprise sterile aqueous preparations of treprostinil or its derivative, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations according to the invention may contain from 0.1 to 5% w/v of active compound and may be administered at a rate of 0.1 ml/min/kg. Alternatively, the invention may administered at a rate of 0.625 to 50 ng/kg/min. Alternatively, the invention may be administered at a rate of 10 to 15 ng/kg/min.

Formulations suitable for oral administration may be presented in discrete units, such as capsules, cachets, lozenges, or tablets, each containing a predetermined amount of treprostinil or its derivative, or a pharmaceutically acceptable salt thereof; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients)

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising treprostinil or its derivative, or a pharmaceutically acceptable salt thereof, in a flavored base, usually sucrose and acacia or tragacanth; and pastilles comprising the compound in an inert base such as gelatin and glycerin or sucrose and acacia.

Formulations suitable for rectal administration are preferably presented as unit dose suppositories. These may be prepared by admixing treprostinil or its derivative, or a pharmaceutically acceptable salt thereof, with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w. Formulations for transdermal administration may be delivered by iontophoresis (see, for example, *Pharmaceutical Research*, 3(6): 318 (1986)) and typically take the form of an optionally buffered aqueous solution of treprostinil or its derivative or salt or thereof. Suitable formulations comprise citrate or bis/tris buffer (pH 6) or ethanol/water and contain from 0.1 to 0.2M active ingredient.

The compounds of the present invention are conveniently prepared by methods the same as or analogous to those described in U.S. Pat. No. 4,306,075, U.S. Pat. No. 6,528,688 and U.S. Pat. No. 6,441,245.

Additional embodiments are within the scope of the invention. For example, in one embodiment, a method for treating or preventing ischemic lesions in a subject, such as a human being, with a disease or condition that causes ischemic lesions comprises administering to a subject in need thereof an effective amount of treprostinil or its derivative, or a pharmaceutically acceptable salt thereof.

In another embodiment, a kit for treatment or prevention of ischemic lesions in a subject with a disease or condition that causes ischemic lesions comprises (i) an effective amount of treprostinil or its derivative, or a pharmaceutically acceptable salt thereof, (ii) one or more pharmaceutically acceptable carriers and/or additives, and (iii) instructions for use in treating or preventing ischemic lesions.

In certain embodiments, the disease or condition that causes ischemic lesions comprises scleroderma, Buerger's disease, Raynaud's disease and/or Raynaud's phenomenon. In one embodiment, the ischemic lesions comprise digital ischemic lesions. In another embodiment of the method, pain or other symptom associated with digital ischemic lesions is reduced, eliminated or prevented. The digital ischemic lesions include finger ulcers and/or necrotic lesions. In one embodiment, the disease or condition that that causes ischemic lesions comprises systemic schlerois.

In certain method embodiments, the treprostinil or its derivative, or a pharmaceutically acceptable salt thereof, is administered subcutaneously, by continuous subcutaneous infusion, intravenously, in an orally available form selected from the group consisting of tablets and capsules, and/or by inhalation. In other embodiments, the effective amount of treprostinil or its derivative, or a pharmaceutically acceptable salt thereof, is at least 1.0 ng/kg of body weight/min.

In certain kit embodiments, the treprostinil or its derivative, or a pharmaceutically acceptable salt thereof, is in a form suitable for subcutaneous administration, continuous subcutaneous infusion, intravenously administration or inhalation. In other kit embodiments, the treprostinil or its derivative, or a pharmaceutically acceptable salt thereof; is in an orally available form selected from the group consisting of tablets and capsules. In another kit embodiment, the effective amount of treprostinil or its derivative, or a pharmaceutically acceptable salt thereof, is at least 1.0 ng/kg of body weight/min.

In certain other method embodiments, the disease or condition that causes ischemic lesions comprises systemic sclerosis, and the ischemic lesions comprise digital ischemic lesions, and continuous administration of treprostinil or its derivative, or a pharmaceutically acceptable salt thereof, promotes the healing of at least one digital ischemic lesion, and reduces or prevents the development of new digital ischemic lesions. In another embodiment, a method for reducing, eliminating or preventing pain and disability associated with ischemic lesions (such as digital ischemic lesions) in a subject with a disease or condition that causes ischemic lesions comprises administering to a subject in need thereof an effective amount of treprostinil or its derivative, or a pharmaceutically acceptable salt thereof. In other embodiments, the subject is a human being, and the disease or condition that causes ischemic lesions comprises Buerger's disease that does not improve with smoking cessation. In another embodiment, the treprostinil or its derivative, or a pharmaceutically acceptable salt thereof, is administered by continuous subcutaneous infusion by an infusion pump.

EXAMPLES

Example 1

Administration of Treprostinil to Humans with Scleroderma Suffering from Digital Ischemic Lesions Scleroderma patients having at least one lesion (i.e., small sore or area of tissue gangrene) present on a hand or finger are dosed with increasing amounts of treprostinil over 12 weeks. The medication is delivered by a small pump that is connected to a catheter placed under the skin. In this manner, increasing dosages of treprostinil are administered to patients by chronic continuous subcutaneous infusion.

Specifically, a 1.0 mg/mL formulation of treprostinil sodium (REMODULIN®) is administered subcutaneously using a standard micro-infusion, positive-pressure infusion pump designed for subcutaneous drug delivery (Mini-Med). Patients receive an initial dose of 2.5 ng/kg/min of study drug. If, in a given patient, a dose of 2.5 ng/kg/min is not tolerated (e.g., persistent headache, nausea, emesis, restlessness, anxiety or severe pain at infusion site that cannot be adequately managed by medication or topical treatment), the dose is reduced to 1.25 ng/kg/min. Patients are maintained at 2.5 ng/kg/min (or 1.25 ng/kg/min if 2.5 ng/kg/min is not tolerated) during Week 1. After that, the dose is raised by 2.50 ng/kg/min each week until not tolerated or once a target dose is reached.

Dosing is increased weekly unless not tolerated by the patient. Weekly dose increases do not exceed 2.50 ng/kg/min each. One example of a target dose is 15 ng/kg/min. The minimum dose is usually not less than 0.625 ng/kg/min. After completion of the Week 12 treatment, drug infusion are terminated by gradual reduction of the infusion rate (over a period of 1-4 hours, as clinically indicated) until a rate of 0 ng/kg/min is reached.

Patients receiving the above-described treatment experience fewer new lesions associated with scleroderma, and see a reduction in the number, size and severity of lesions present before treatment. The administration of treprostinil treats and prevents digital ischemic lesions in patients with systemic sclerosis.

Example 2

Study of Treprostinil (Remodulin®) for the Treatment and Prevention of Digital Ischemic Lesions in Patients with Systemic Sclerosis Digital ischemic lesions (DIL) occur in up to 35% of patients with systemic sclerosis and are exquisitely painful, often progressing to necrosis requiring amputation. The purpose of this study was to evaluate the effect of treprostinil on the healing and prevention of DIL in patients with systemic sclerosis.

TABLE 1

| | Baseline Patient Demographics | | | | |
| --- | --- | --- | --- | --- | --- |
| | Patient | | | | |
| | 1 | 2 | 3 | 4 | 5 |
| Age (years) | 36 | 63 | 48 | 52 | 41 |
| Gender | Female | Female | Female | Female | Female |
| Limited v. Diffuse | Diffuse | Diffuse | Diffuse | Diffuse | Diffuse |

TABLE 1-continued

Baseline Patient Demographics

| | Patient | | | | |
|---|---|---|---|---|---|
| | 1 | 2 | 3 | 4 | 5 |
| Disease Duration (years) | 5.1 | 14.2 | 1.7 | 1.7 | 1.7 |
| Smoking History | Never | Never | Current | Remote§ | Current |
| Antiphospholipid Antibodies | Yes | No | No | No | No |
| Other Risk Factors for Vasculopathy* | None | None | None | None | None |
| Concomitant Medications for Scleroderma (stable throughout study) | Nifedipine Losartan | Methotrexate Diltiazem Meloxicam Prednisone | Losartan Minocycline | Lisinopril Penicillamine Minocycline Celecoxib | None |
| Number of DIL | 5 | 25 | 3 | 7 | 9 |
| Size of Target Lesion (mm) | 7 | 10 | 10 | 5 | 5 |

§Remote history of smoking if quit greater than 10 years ago.
*Risk factors assessed for at screening included a history of sickle cell disease. lymphoma, leukemia, myeloma, paraproteinemia, cryoglobulinemia. Cryofibrinogenemia, hepatitis C infection, or diabetes mellitus.

Methods:

This study involved 12 subjects with diffuse or limited scleroderma with at least one DIL that had been present for 2 months or more (Table 1). Subjects who completed the study were treated for 12 weeks with treprostinil and followed for another 8 weeks after drug discontinuation (FIG. 1).

TABLE 2

Adverse Events in All Patients Enrolled

| Adverse Event | Number of Patients |
|---|---|
| Injection Site Reaction§ | 12 |
| Mild | 6 |
| Moderate* | 1 |
| Severe** | 5 |
| Menstrual irregularities | 1 |
| Dizziness | 3 |
| Headache | 2 |
| Chills | 1 |
| Pruritus | 2 |
| Diarrhea | 2 |
| Nausea/Vomiting | 3 |
| Jaw Pain | 1 |
| Digital Amputation** | 2 |

§All patients used pimecrolimus cream prior to injection and every 12 hours for injection site prophylaxis and treatment
*Required intermittent dosing schedule
**Resulted in discontinuation from trial treprostinil (Remodulin®) was delivered to the subjects by continuous subcutaneous infusion, beginning at a rate of infusion of 2.5 ng/kg/min, which was increased by 2.5 ng/kg/min each week until a maximum rate of 15 ng/kg/min was achieved. Assessments were performed at baseline, weeks 2, 6, 12, 16, and 20. At each visit, the largest (target) lesion and other prominent DIL were measured by recording the largest diameter of the lesions. DIL were counted and photographed. Patient and physician global assessment of ulcers as well as patient assessment of disability from DIL were measured using visual analogue scales (VAS) at each visit.

Results:

Three of the 12 subjects completed the study and two are currently still enrolled (FIG. 2). Two subjects discontinued the study for surgical treatment of previously ischemic digits, and five subjects were unable to complete the study due to intolerable injection site pain (FIG. 2).

Of the four subjects who completed 12 weeks of active therapy, target lesions improved in all patients, and three experienced complete resolution of their target lesions (FIG. 3). On average there was a 65% decrease in the size of baseline DIL (FIG. 4). No new ulcers developed in any patients while receiving continuous treprostinil therapy (FIG. 5); however, two of three patients developed new ulcers during the 8-week follow-up period after drug discontinuation. By week 6, all five subjects demonstrated marked improvements in subjective measures of severity of their DIL according to patient and physician global assessment and DIL disability VAS scores. Physician global assessment of DIL severity improved on average by 60% after 12 weeks of therapy (FIGS. 6 and 7). Patient global assessment and DIL disability VAS scores improved on average by 89% and 77% respectively by week 12 (FIGS. 6 and 7).

Conclusion:

This study indicates that continuous subcutaneous treprostinil therapy is useful in the treatment and prevention of DIL in patients with systemic sclerosis. Continuous treprostinil therapy promotes healing of DIL, and is useful in preventing the development of new DIL. The treprostinil therapy also reduces pain and disability associated with DIL.

Example 3

Treprostinil Sodium Provides Symptom Relief in Severe Buerger's Disease

Background

Buerger's disease (thromboangiitis oliterans or TAO) is a clinical syndrome characterized by the development of segmental thrombotic occlusions of the medium and small arteries. The disease is clinically and pathologically distinguishable from atherosclerotic disease. Histopathology features may vary with the duration of the disease. In the chronic or end stage phase of the disease, only organized thrombus and fibrosis of the blood vessel is seen. In all stages of the disease, the normal structure of the vessel wall generally remains intact. Angiographic features of Buerger's disease are the involvement of small and medium sized vessels, segmental occlusive lesions, more severe disease distally and collateralization around areas of occlusion (corkscrew collaterals). Olin, Jeffery W., Current Concepts: Thromboangiitis Obliterans (Buerger's Disease), N. Engl. J. Med., Volume 343(12), 864-869 (Sep. 21, 2000).

It is typically seen in young men who are heavy smokers and is more common in Asian and eastern European countries than in the US. Smoking is generally considered a requirement for diagnosis. Proposed clinical diagnostic criteria are: 1) smoking history, 2) onset before the age of 50 years; 3) infra-popliteal arterial occlusions; 4) either upper limb involvement or phlebitis migrans; and 5) absence of atherosclerotic risk factors other than smoking. Shionoya, Shigehiko Diagnostic criteria of Buerger's Disease, International Journal of Cardiology 66 (Suppl. 1) S243-S245 (1998).

The primary treatment for Buerger's disease is cessation of cigarette smoking. Persistent or recurrent symptoms occur rarely in patients who quit smoking and maintain a tobacco free environment to exclude any second-hand smoke. In patients whose disease progresses despite smoking cessation, therapeutic options are limited. Revascularization is rarely indicated and usually not successful because of the diffuse and distal distribution of the disease. Mills, Jopseph L Sr. Buerger's Disease in the 21$^{st}$ Century: Diagnosis, Clinical Features, and Therapy, Seminars in Vascular Surgery, Vol. 16(3), 179-189 (September 2003).

treprostinil sodium (Remodulin®) is a stable analogue of prostacyclin with a plasma half life of more than 4 hours and is approved in the U.S. for chronic, continuous subcutaneous (SC) infusion in patients with pulmonary arterial hypertension (PAH). This case illustrates an example of a patients with severe and progressive Buerger's disease treated with a continuous subcutaneous infusion of treprostinil sodium in whom there were no other therapeutic options available.

Case Report

A 42 year old Cuban male was first seen in 2002 for evaluation of ischemic pain of his right hand. The patient had a complicated medical history of bilateral foot gangrene resulting in a left BKA (below the knee amputation) in 1991 and a right BKA in 1993. His only risk factor was a long history of heavy cigarette smoking. He began to experience right hand pain in 2002. An arteriogram revealed right hand ischemia with few distal targets amenable for revascularization. A trial of thrombolytic therapy was attempted, but abandoned 48 hours later and the patient was discharged on warfarin. Because of recurrent ischemic ulcers and arm claudication, the patient sought additional opinions by several other vascular specialists and was told nothing could be done.

The patient's condition was diagnosed in 2002 as Buerger's disease. This patient met all the Buerger's diagnostic criteria with the exception of a positive history of hyperlipidemia which had not been present at the time he first developed symptoms. Review of systems was negative for connective tissue disease. On physical examination, both brachial pulses were palpable but bilateral radial and ulnar pulses were absent. There was evidence of chronic ischemic changes in the right hand with loss of the digital fat pads. Aliens test was abnormal bilaterally. There was a small area of necrosis beneath the nail of the right thumb. There was another ischemic necrotic ulcer in the distal phalanx of the right middle finger just proximal to the nail which measured 1 cm in length. Both hands turned completely white and the patient would complain of pain with elevation of the arms.

The patient had a long history of smoking but quit in 2002 when his claudication and ischemic symptoms recurred. He has no history of diabetes or hypertension. He is a recovering alcoholic but denies illicit drug use. There is no family history of thrombotic disorders, or hypercoagulable disorders. Laboratory findings were negative for connective tissue diseases. A hypercoagulable lab panel, including factor V Leiden, antithrombin III, protein C, protein S, prothrombin gene mutation, anticardiolipin antibody, and lupus anticoagulant, was unremarkable.

Cilostazol was added to pentoxifylline, simvastatin and narcotic analgesics but symptoms did not improve. In December 2002, his right index finger was amputated due to gangrene. At follow-up, there was still significant necrosis and ulceration of the right thumb. The patient was referred to Anesthesia and underwent several stellate ganglion blocks, again with no reported change in symptoms. Eventually, the right thumb required amputation. He was lost to follow-up (i.e. was under another health care provider and the details of what happened during this period are unknown) for a short period of time and an ulcer that developed on the right index finger became infected and subsequently amputated.

Soon after, the patient exhibited disabling claudication symptoms primarily manifest as weakness in both arms, especially the left, and unable to carry out simply activities of daily living such as dressing himself or combing his hair. The right middle finger ulcer was not healing.

Noninvasive vascular testing revealed flat tracings in both upper extremities at the digital level with the left worse than the right. An arteriogram showed occluded right brachial artery at the elbow with severe distal disease and an occluded left brachial artery at the takeoff from the axiliiary artery with severe disease of the left hand. The arteriogram demonstrated "corkscrew collaterals" at several levels. It was felt that the patient might benefit from revascularization and a left axillary brachial artery bypass using human umbilical vein was performed. Despite therapeutic anticoagulation, the bypass went on to occlude.

At this point, subcutaneous treprostinil therapy was administered to the patient. Treprostinil was delivered chronically by continuous subcutaneous infusion using a pager-sized ambulatory infusion pump (Medtronic Minimed 407C, Minneapolis, Minn.)). In September 2003, treprostinil was started at 2.5 ng/kg/min and titrated by 1 ng/kg/min every 7 days until the patient reached his maximum tolerated dose of 12.5 ng/kg/min and was continued for the next 10 months. He was unable to tolerate higher doses due to diarrhea and jaw pain, commonly reported dose limiting side effects of prostacyclin therapy. The patient has reported improved comfort and increased ability to participate in activities of daily living such as dressing self, combing his hair, reaching above his head and driving. Doppler studies demonstrated improvement in pulse volume recording wave form. Attempts to discontinue treprostinil resulted in return of ischemic symptoms within 1 week. The patient is now on a maintenance dose of treprostinil 12 ng/kg/min from 9 PM-9 AM every seven day, with no drug for the next 7 days. The patient has had sustained relief of symptoms on this regimen including complete healing of the ulcer on his right middle finger.

The patient's symptomatic improvements appear to be related to treprostinil infusion. The patient's disease continued to progress despite quitting smoking in early 2002. We confirmed the patient was smoke free with a negative cotinine urine test in 2003 at the time he was started on treprostinil. There has been continued improvement in pain and digital ulcer healing and an overall improvement in his quality of life. While there are no formal dosing recommendations from the manufacturer, our dosing regimen including the maintenance dosing appears safe and effective based on clinical improvement.

These results suggest that subcutaneous treprostinil therapy is clinically useful in Buerger's disease that does not improve with smoking cessation, particularly in the presence of critical limb ischemia where other therapeutic options have failed. The ease of the application, similar to insulin pumps, make it an attractive therapeutic option versus more invasive intravenous delivery and is well tolerated It will apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A method for treating peripheral ischemic lesions on the skin of a subject, comprising administering to a subject in need thereof an effective amount of treprostinil or its derivative, or a pharmaceutically acceptable salt thereof, wherein said derivative is an inhaled form of treprostinil or an oral form of treprostinil.

2. The method of claim 1, wherein the ischemic lesions are caused by at least one of scleroderma, Buerger's disease, Raynaud's disease and Raynaud's phenomenon.

3. The method of claim 1, wherein the ischemic lesions comprise digital ischemic lesions.

4. The method of claim 3, wherein the digital ischemic lesions comprise finger ulcers and/or necrotic lesions.

5. The method of claim 1, wherein the ischemic lesions are caused by systemic sclerosis.

6. The method of claim 3, wherein pain associated with the digital ischemic lesions in the subject is reduced.

7. The method of claim 1, wherein said administering comprises administering a pharmaceutically acceptable salt of treprostinil.

8. The method of claim 1, wherein the subject is a human being.

9. The method of claim 1, wherein said administering is performed subcutaneously.

10. The method of claim 1, wherein said administering is performed by continuous subcutaneous infusion.

11. The method of claim 1, wherein said administering is performed intravenously.

12. The method of claim 1, wherein said administering is performed orally.

13. The method of claim 1, wherein said administering is performed by inhalation.

14. The method of claim 1, wherein the effective amount is at least 1.0 ng/kg of body weight/min.

15. The method of claim 1, wherein the ischemic lesions are caused by systemic sclerosis, wherein the ischemic lesions comprise digital ischemic lesions, wherein said administering is continuous administration and wherein said administering promotes healing of at least one of the digital ischemic lesions, and reduces the development of new digital ischemic lesions.

16. A method for reducing pain associated with peripheral ischemic lesions comprising administering to a subject in need thereof an effective amount of treprostinil or its derivative, or a pharmaceutically acceptable salt thereof, wherein said derivative is inhaled form of treprostinil or and oral form of treprostinil.

17. The method of claim 16, wherein the ischemic lesions comprise digital ischemic lesions.

18. The method of claim 2, wherein the subject is a human being with Buerger's disease that does not improve with smoking cessation.

19. The method of claim 1, wherein said administering is performed by continuous subcutaneous infusion by an infusion pump.

20. The method of claim 5, wherein said administering comprises orally administering to the subject an oral formulation comprising diethanolamine salt of treprostinil.

21. The method of claim 20, wherein said ischemic lesions comprise digital ischemic lesions.

22. The method of claim 21, wherein said administering promotes the healing of at least one of the digital ischemic lesions, and reduces the development of new digital ischemic lesions.

23. The method of claim 12, wherein said administering comprises administering to the subject an oral formulation comprising diethanolamine salt of treprostinil.

24. The method of claim 23, wherein said formulation is in a form selected from the group consisting of tablets and capsules.

25. The method of claim 16, wherein said administering comprises administering orally to the subject an oral formulation comprising diethanolamine salt of treprostinil.

26. A method of treating critical limb ischemia comprising administering to a subject in need thereof an effective amount of treprostinil or its derivative, or a pharmaceutically acceptable salt thereof, wherein said derivative is an inhaled form of treprostinil or an oral form of treprostinil.

27. The method of claim 26, wherein said administering reduces rest pain associated with the critical limb ischemia in the subject.

28. The method of claim 26, wherein said administering results in healing ischemic lesions in the subject.

29. The method of claim 28, wherein said ischemic lesions comprise digital ischemic lesions.

30. The method of claim 29, wherein the digital ischemic lesions comprise finger ulcers and/or necrotic lesions.

31. The method of claim 26, wherein said administering comprises administering a pharmaceutically acceptable salt of treprostinil.

32. The method of claim 26, wherein said administering is performed subcutaneously.

33. The method of claim 26, wherein said administering is performed by continuous subcutaneous infusion.

34. The method of claim 26, wherein said administering is performed intravenously.

35. The method of claim 26, wherein said administering is performed orally.

36. The method of claim 35, wherein said administering comprises administering to the subject an oral formulation comprising diethanolamine salt of treprostinil.

37. The method of claim 35, wherein said formulation is in a form selected from the group consisting of tablets and capsules.

38. The method of claim 26, wherein said administering is performed by inhalation.

39. The method of claim 26, wherein the effective amount is at least 1.0 ng/kg of body weight/min.

40. The method of claim 26, wherein said administering is performed by continuous subcutaneous infusion by an infusion pump.

41. The method of claim 26, wherein the subject is a human being.

* * * * *